United States Patent
You et al.

(10) Patent No.: US 11,046,705 B1
(45) Date of Patent: Jun. 29, 2021

(54) METHOD FOR PREPARING ETODOLAC METHYL ESTER

(71) Applicant: Zhejiang International Studies University, Hangzhou (CN)

(72) Inventors: Jinzong You, Hangzhou (CN); Yingfei Li, Hangzhou (CN); Deqiang Qi, Hangzhou (CN); Chengjie Wu, Hangzhou (CN)

(73) Assignee: ZHEJIANG INTERNATIONAL STUDIES UNIVERSITY, Zhejiang (CN)

( * ) Notice: Subject to any disclaimer, the term of this patent is extended or adjusted under 35 U.S.C. 154(b) by 0 days.

(21) Appl. No.: 16/929,670

(22) Filed: Jul. 15, 2020

(30) Foreign Application Priority Data

Mar. 18, 2020 (CN) .......................... 202010191605.9

(51) Int. Cl.
   *C07D 491/052* (2006.01)
(52) U.S. Cl.
   CPC ................ *C07D 491/052* (2013.01)
(58) Field of Classification Search
   None
   See application file for complete search history.

(56) References Cited

U.S. PATENT DOCUMENTS 4,585,877 A    4/1986   Demerson et al.

FOREIGN PATENT DOCUMENTS

JP    2009120599    6/2009

OTHER PUBLICATIONS

Zhao, Li-Hua, et al., Synthesis of Etodolac, Chinese Journal of Pharmaceuticals 2005, 36 (12), 730-731 (2 pages).

*Primary Examiner* — Samantha L Shterengarts
(74) *Attorney, Agent, or Firm* — McCracken & Gillen LLC

(57) ABSTRACT

The present invention discloses a method for preparing etodolac methyl ester, and relates to the technical field of organic synthesis. The method provided in the present invention includes the following steps: (1) raw materials are mixed and subjected to cyclization reaction at 20° C. to 25° C. to obtain a reaction solution, where the raw materials include 7-ethyltryptophol, methyl 3-oxopentanoate, trimethylhalosilane and methanol, excluding concentrated sulfuric acid, and the trimethylhalosilane is trimethylchlorosilane or trimethylbromosilane; and (2) the reaction solution is cooled to 10° C. to 15° C., and then filtered to obtain etodolac methyl ester and a mother liquor. The method provided in the present invention has a high yield, and does not use concentrated sulfuric acid that is extremely harmful and tends to cause product oxidation.

14 Claims, No Drawings

METHOD FOR PREPARING ETODOLAC METHYL ESTER

CROSS-REFERENCE TO RELATED APPLICATIONS

The present application claims benefit of You, et al., Chinese Patent Application 202010191605.9, entitled "METHOD FOR PREPARING ETODOCAL METHYL ESTER" and filed Mar. 18, 2020. The entire contents of this application are incorporated herein by reference.

TECHNICAL FIELD

The present invention relates to the technical field of organic synthesis, and in particular to a method for preparing etodolac methyl ester.

BACKGROUND

Etodolac methyl ester (compound 1) is a key intermediate for etodolac (compound 2). Etodolac, a nonsteroidal anti-inflammatory drug of pyrancarboxylic acid, is used clinically to moderate pain and fever. Etodolac is produced by the alkaline hydrolysis of etodolac methyl ester and then acid adjustment, and the specific process can be seen in formula 1 [references: 1, U.S. Pat. No. 4,585,877 (1986), 2, Chinese Journal of Pharmaceuticals, 32 (2), 730-731, 2005]:

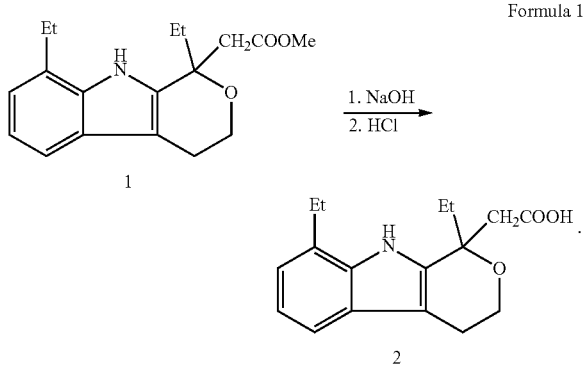

Formula 1

Industrially, etodolac methyl ester is generally prepared by the dehydration of 7-ethyltryptophol (compound 3) and methyl 3-oxopentanoate (compound 4) under catalysis, and the specific process can be seen in formula 2:

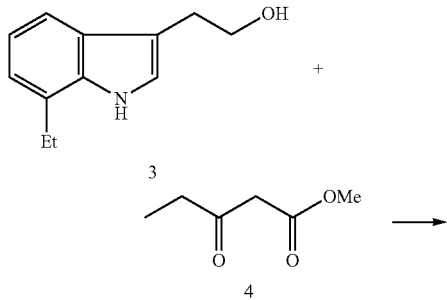

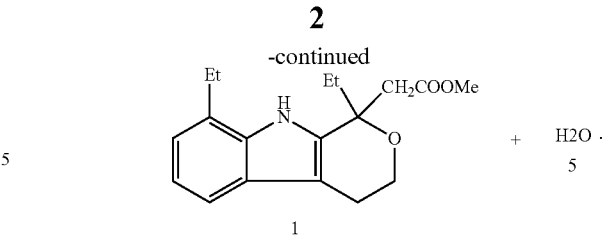

Formula 2

Existing methods for preparing etodolac methyl ester can been found in the following references: 1. Japanese patent JP2009120599, where, in Example 1, etodolac methyl ester is prepared by adopting 7-ethyltryptophol and methyl 3-oxopentanoate as raw materials and acetonitrile including concentrated sulfuric acid as a solvent; and in Examples 2 to 6, etodolac methyl ester is prepared under the same conditions as that in Example 1, except that the type and amount of solvent, the type and amount of the acid, the reaction time and the reaction temperature are changed, with a maximum yield of 94.7%. In addition to the extremely-harmful concentrated sulfuric acid, this process also adopts highly-toxic acetonitrile that tends to cause intoxication if inhaled, eaten or absorbed via skin. Therefore, this process is not conducive to the health of workers and thus not suitable for industrial production. 2. Chinese Journal of Pharmaceuticals, 2005, 32 (2), 730-731, where, etodolac methyl ester is prepared in a mixed solvent of methanol and toluene by adopting 7-ethyltryptophol and methyl 3-oxopentanoate as raw materials and concentrated sulfuric acid as a catalyst and dehydrating agent, with a yield of 82.7%. The process has a low yield, and also adopts extremely-harmful concentrated sulfuric acid.

Above methods, adopting 7-ethyltryptophol and methyl 3-oxopentanoate as raw materials and concentrated sulfuric acid as a dehydrating agent, are main methods for preparing etodolac methyl ester industrially. However, these methods will impose large waste acid pollution, and the concentrated sulfuric acid tends to cause the impurity of etodolac methyl ester (a nitrogen-including product) due to oxidation, and thus compromises the appearance of the product.

SUMMARY

In view of this, the present invention is intended to provide a method for preparing etodolac methyl ester. In the present invention, etodolac methyl ester (compound 1) is prepared by adopting 7-ethyltryptophol (compound 3) and methyl 3-oxopentanoate (compound 4) as raw materials, methanol as a solvent, and trimethylhalosilane (compound 6) as a dehydrating agent and catalyst.

The preparation method provided in the present invention does not use concentrated sulfuric acid that is extremely harmful and tends to cause product oxidation, and has a high yield.

To achieve the above purpose, the present invention provides the following technical solution.

A method for preparing etodolac methyl ester includes the following steps:
(1) raw materials are mixed and subjected to cyclization reaction at 20° C. to 25° C. to obtain a reaction solution, where the raw materials include 7-ethyltryptophol, methyl 3-oxopentanoate, trimethylhalosilane and methanol, excluding concentrated sulfuric acid, and the trimethylhalosilane is trimethylchlorosilane or trimethylbromosilane; and (2) the reaction solution is cooled to 10° C. to 15° C., and then filtered to obtain etodolac methyl ester and a mother liquor.

Preferably, the mixing in step (1) is conducted by adding trimethylhalosilane dropwise to a mixed solution of 7-ethyltryptophol, methyl 3-oxopentanoate and methanol at 15° C. to 20° C.

Preferably, the dropwise adding is performed at a rate of 20% to 30% of the total amount of trimethylhalosilane per hour.

Preferably, in step (1), 7-ethyltryptophol, methyl 3-oxopentanoate and trimethylhalosilane are used at a mole ratio of 1:(1-1.3):(1-1.3).

Preferably, in step (1), the cyclization reaction is conducted for 15 h to 18 h.

Preferably, after a mother liquor is obtained in step (2), the method further includes: subjecting the mother liquor to post-treatment to obtain etodolac methyl ester; or recycling the mother liquor in step (1).

Preferably, the post-treatment includes the following steps:
(a) the mother liquor is concentrated and then slurried with methanol at 30° C. to 45° C. to obtain a slurry; and
(b) the slurry is cooled to 10° C. to 15° C., and then filtered to obtain etodolac methyl ester.

Preferably, after the filtering in step (2) and step (b), the method further independently includes: rinsing and drying the obtained solid to obtain etodolac methyl ester, where the rinsing is conducted with methanol, a sodium bicarbonate aqueous solution and water in sequence.

Preferably, after the solid obtained in step (2) is rinsed with methanol, the resulting rinse solution is added to the mother liquor.

Preferably, the trimethylhalosilane is recovered by the following method:
the mother liquor is neutralized to neutrality and then subjected to rectification to obtain hexamethyldisiloxane; and the hexamethyldisiloxane is mixed with hydrogen halide for halogenation to obtain trimethylhalosilane, where the hydrogen halide is hydrogen chloride or hydrogen bromide.

The present invention provides a method for preparing etodolac methyl ester, and the method includes the following steps: (1) raw materials are mixed and subjected to cyclization reaction at 20° C. to 25° C. to obtain a reaction solution, where the raw materials include 7-ethyltryptophol, methyl 3-oxopentanoate, trimethylhalosilane and methanol, excluding concentrated sulfuric acid, and the trimethylhalosilane is trimethylchlorosilane or trimethylbromosilane; and (2) the reaction solution is cooled to 10° C. to 15° C., and then filtered to obtain etodolac methyl ester and a mother liquor. In the present invention, etodolac methyl ester is prepared by adopting 7-ethyltryptophol and methyl 3-oxopentanoate as raw materials, methanol as a solvent, and trimethylhalosilane as a dehydrating agent and catalyst. The preparation method provided in the present invention does not use concentrated sulfuric acid that is extremely harmful and tends to cause product oxidation, and has a high yield.

Moreover, the present invention further improves the product yield by continuously recycling the mother liquor, and can achieve almost quantitative yield (meaning that the reaction can be completed more than 99.9%, which can be regarded as a complete reaction). The workload of solvent treatment is reduced, resulting in simple operations.

Further, the method provided in the present invention recovers trimethylhalosilane by performing neutralization, rectification and halogenation on the mother liquor in sequence, and trimethylhalosilane is easy to be recycled.

DETAILED DESCRIPTION

The present invention provides a method for preparing etodolac methyl ester, and the method includes the following steps:
(1) raw materials are mixed and subjected to cyclization reaction at 20° C. to 25° C. to obtain a reaction solution, where the raw materials include 7-ethyltryptophol, methyl 3-oxopentanoate, trimethylhalosilane and methanol, excluding concentrated sulfuric acid, and the trimethylhalosilane is trimethylchlorosilane or trimethylbromosilane; and
(2) the reaction solution is cooled to 10° C. to 15° C., and then filtered to obtain etodolac methyl ester and a mother liquor.

In the present invention, raw materials are mixed and subjected to cyclization reaction at 20° C. to 25° C. to obtain a reaction solution. The raw materials include 7-ethyltryptophol, methyl 3-oxopentanoate, trimethylhalosilane and methanol, excluding concentrated sulfuric acid, and the trimethylhalosilane is trimethylchlorosilane or trimethylbromosilane. In the present invention, the mixing is conducted preferably by adding trimethylhalosilane dropwise to a mixed solution of 7-ethyltryptophol, methyl 3-oxopentanoate and methanol at 15° C. to 20° C. and then subjecting the resulting mixture to cyclization reaction at 20° C. to 25° C. The present invention has no special requirement for the mixing method of 7-ethyltryptophol, methyl 3-oxopentanoate and methanol, and a method well known in the art can be used, specifically, for example, stirring and mixing. In the present invention, the trimethylhalosilane is added dropwise at a rate preferably of 20% to 30% of the total amount of trimethylhalosilane per hour.

In the present invention, 7-ethyltryptophol, methyl 3-oxopentanoate and trimethylhalosilane are used at a molar ratio preferably of 1:(1-1.3):(1-1.3), and more preferably of 1:1.1:1.1. The present invention has no special requirement for the sources of 7-ethyltryptophol, methyl 3-oxopentanoate and trimethylhalosilane, and commercially available products well known to those skilled in the art may be used. In the present invention, the methanol is added at an amount preferably 3 times the mass of 7-ethyltryptophol.

In the present invention, the cyclization reaction is conducted at 20° C. to 25° C., and preferably at 21° C. to 24° C.; and the cyclization reaction is conducted preferably for 15 h to 18 h, more preferably for 18 h, and specifically until 7-ethyltryptophol has a content preferably less than 0.1% in the reaction solution, as measured by HPLC. Hexamethyldisiloxane is produced from trimethylhalosilane by the cyclization reaction. In the present invention, the cyclization reaction has a reaction formula shown as formula 3 (X in formula 3 is Cl or Br):

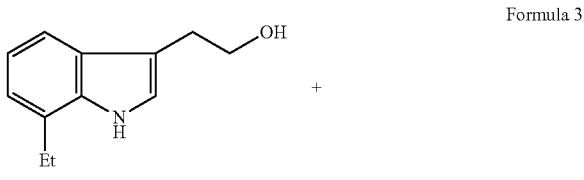

Formula 3

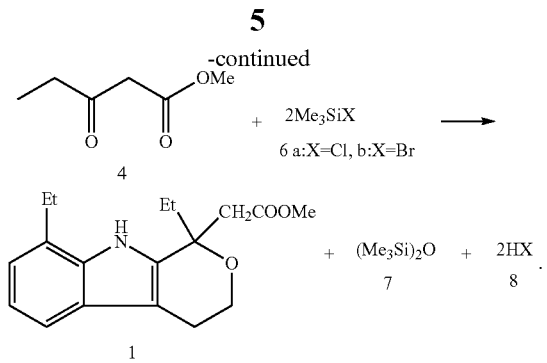

In the present invention, the obtained reaction solution is cooled to 10° C. to 15° C., and then filtered to obtain etodolac methyl ester and a mother liquor. In the present invention, before the filtering, the reaction liquid is preferably stored at 10° C. to 15° C. for 1 h to allow the product to be completely precipitated.

The present invention has no special requirement for the filtering method, and a method well known in the art can be used. In the present invention, after the filtering, the obtained solid is preferably further rinsed and dried to obtain etodolac methyl ester. In the present invention, the rinsing is preferably conducted with methanol, a sodium bicarbonate aqueous solution and water in sequence, and the sodium bicarbonate aqueous solution has a mass concentration preferably of 5%. The present invention has no special requirement for the number of rinsings, provided that the etodolac methyl ester is cleaned. In the present invention, after the obtained solid is rinsed with methanol, the resulting rinse solution is preferably added to the mother liquor, that is, the mother liquor preferably includes a filtrate obtained from the filtering of the reaction solution and a rinse solution obtained from the rinsing with methanol. The drying method is not particularly limited in the present invention, and a technical solution of drying well known to a person skilled in the art may be employed. In the present invention, the drying is conducted preferably at 80° C. to 100° C., and preferably for 6 h to 8 h. In the embodiment of the present invention, the yield of etodolac methyl ester is calculated as 92.4% to 92.5%, based on the weight of etodolac methyl ester methyl after rinsing and drying.

In the present invention, after a mother liquor is obtained, the method further includes: subjecting the mother liquor to post-treatment to obtain etodolac methyl ester; and
recycling the mother liquor in step (1).

In the present invention, when the mother liquor is preferably subjected to a post-treatment to obtain etodolac methyl ester, the post-treatment preferably includes the following steps:
(a) the mother liquor is concentrated and then slurried with methanol at 30° C. to 45° C. to obtain a slurry; and
(b) the slurry is cooled to 10° C. to 15° C., and then filtered to obtain etodolac methyl ester.

In the present invention, the mother liquor is concentrated and then slurried with methanol at 30° C. to 45° C. to obtain a slurry. The present invention has no special requirement for the concentration method, and a method well known in the art can be used, specifically, such as reduced-pressure distillation. In the present invention, the concentration is conducted until the mother liquor has no flow. In the present invention, the slurrying is conducted preferably at 40° C. The present invention has no special requirement for the specific slurrying method, and a method well known in the art can be used. In the present invention, the slurrying is conducted preferably for 1 h.

In the present invention, after a slurry is obtained, the slurry is cooled to 10° C. to 15° C., and then filtered to obtain etodolac methyl ester. In the present invention, before the filtering of the slurry, the slurry is preferably stored at 10° C. to 15° C. for 1 h to allow the product to be completely precipitated. The present invention has no special requirement for the filtering method, and a method well known in the art can be used. In the present invention, after the filtering, the obtained solid is preferably further rinsed and dried to obtain etodolac methyl ester. In the present invention, the rinsing is preferably conducted with methanol, a sodium bicarbonate aqueous solution and water in sequence, and the sodium bicarbonate aqueous solution has a mass concentration preferably of 5%. The present invention has no special requirement for the number of rinsings, provided that the etodolac methyl ester is cleaned. In the present invention, the drying is conducted preferably at 80° C. to 100° C., and preferably for 6 h to 8 h. In the embodiment of the present invention, the yield of etodolac methyl ester is calculated as 97.9% to 98.0%, based on the combined weight of etodolac methyl ester obtained from the reaction solution by filtering, rinsing and drying, and etodolac methyl ester obtained from the treatment of the mother liquor.

The mother liquor is preferably recycled in step (1) preferably in the following manner: at 15° C. to 20° C., the mother liquor is mixed with 7-ethyltryptophol, methyl 3-oxopentanoate and methanol, and then trimethylhalosilane is added dropwise; the reaction described in step (1) is performed at 20° C. to 25° C.; and then the operation in step (2) is performed. The mother liquor is recycled in this cycle. In a specific embodiment of the present invention, the mother liquor can be recycled 1 or 2 times. The present invention can further improve the product yield by continuously recycling the mother liquor, and can achieve almost quantitative yield. The workload of solvent treatment is reduced, resulting in simple operations. In a specific embodiment of the present invention, the mother liquor is recycled once, and the product yield is 99.7% to 99.9%; and the mother liquor is recycled twice, and the product yield is 99.9% to 100.1%.

In the present invention, there is hexamethyldisiloxane in the mother liquor, which is a by-product from the reaction of trimethylhalosilane. In the present invention, trimethylhalosilane is preferably recovered by the following method: the mother liquor is neutralized to neutrality and then subjected to rectification to obtain hexamethyldisiloxane $(Me_3Si)_2O$; and the hexamethyldisiloxane is mixed with hydrogen halide for halogenation to obtain trimethylhalosilane, where the hydrogen halide is hydrogen chloride or hydrogen bromide. The reaction process for recovering trimethylhalosilane is shown as formula 4:

Formula 4

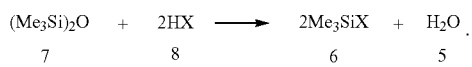

In the present invention, etodolac methyl ester is prepared by adopting 7-ethyltryptophol and methyl 3-oxopentanoate as raw materials, methanol as a solvent, and trimethylhalosilane as a dehydrating agent and catalyst. The preparation method provided in the present invention has a high yield, and does not use concentrated sulfuric acid that is extremely harmful and tends to cause product oxidation. Moreover, trimethylhalosilane is easy to be recycled.

The method for preparing etodolac methyl ester provided in the present invention are described in detail below with reference to examples, but the examples cannot be understood as limiting the protection scope of the present invention.

Example 1

Trimethylchlorosilane was used as catalyst and dehydrating agent.

At 18° C., 283.5 g of methanol, 96.4 g of 7-ethyltryptophol (content: 98.0%, scalar quantity: 0.5 mol) and 71.5 g of methyl 3-oxopentanoate (0.55 mol) were added to a four-necked flask equipped with a thermometer, a mechanically-agitated drying tube and a constant-pressure dropping funnel. 59.7 g of trimethylchlorosilane (0.55 mol) was added to the constant-pressure dropping funnel, and then slowly added dropwise to the above reaction system at a controlled temperature no more than 20° C. for 4 h. After the dropwise addition was completed, the reaction system reacted overnight (about 18 h) at 22° C. until the content of 7-ethyltryptophol was less than 0.1%, as measured by HPLC. Then the reaction solution was cooled to 12° C. and kept at this temperature for 1 h, and filtered. The filter cake was rinsed with 25 g of cold methanol (10° C.), and the mother liquor was to be treated.

The filter cake was rinsed with 150 g of 5% sodium bicarbonate solution and 50 g of water, and dried to obtain a white solid product: 138.9 g, HPLC purity: 99.82%, yield: 92.3%, melting point: 130.9° C. to 131.3° C.

Structural Identification of the Product:

HNMR ($^1$H-NMR) (CDCl$_3$, 500 MHz): δ 0.83 (t, 3H, CH$_3$), 1.39 (t, 3H, CH$_3$), 2.00 (q, 1H, ½CH$_2$), 2.17 (q, 1H, ½CH$_2$), 2.73-3.04 (m, 6H, 3CH$_2$), 3.72 (s, 3H, OCH$_3$), 3.91-4.07 (m, 2H, CH$_2$), 7.00-7.37 (m, 3H, ph-H), 9.05 (s, 1H, NH), mass spectrum (ESI-MS): 302 (M+1), elemental analysis (C$_{18}$H$_{23}$NO$_3$, %) (measured value/calculated value): C, 71.70/71.73; H, 7.75/7.69; N, 4.58/4.65, infrared spectrum (IR, KBr, cm$^{-1}$): 3381, 2966, 1708, 1444, 1315, 1236, 1175, 1078, 1016, 912, 744.

The mother liquor was concentrated to no flow, slurried with 40 g of methanol at 40° C. for 1 h, cooled to 12° C. and kept at this temperature for 1 h, and filtered. The filter cake was rinsed with 2.5 g of cold methanol, 15 g of 5% sodium bicarbonate solution and 5 g of water, and then dried to obtain a white solid product: 8.5 g, HPLC purity: 99.68%, melting point: 130.8° C. to 131.5° C.

The combined production was 147.4 g, with a yield of 97.9%.

Example 2

Trimethylchlorosilane was used as catalyst and dehydrating agent, and the mother liquor was recycled.

(1) The First Batch of Materials

At 18° C., 283.5 g of methanol, 96.4 g of 7-ethyltryptophol (content: 98.0%, scalar quantity: 0.5 mol) and 71.5 g of methyl 3-oxopentanoate (0.55 mol) were added to a four-necked flask equipped with a thermometer, a mechanically-agitated drying tube and a constant-pressure dropping funnel. 59.7 g of trimethylchlorosilane (0.55 mol) was added to the constant-pressure dropping funnel, and then slowly added dropwise to the above reaction system at a controlled temperature no more than 20° C. for 4 h. After the dropwise addition was completed, the reaction system reacted overnight (about 18 h) at 22° C. until the content of 7-ethyltryptophol was less than 0.1%, as measured by HPLC. Then the reaction solution was cooled to 12° C. and kept at this temperature for 1 h, and filtered. The filter cake was rinsed with 25 g of cold methanol (10° C.), and the mother liquor was to be treated.

The filter cake was rinsed with 150 g of 5% sodium bicarbonate solution and 50 g of water, and dried to obtain a white solid product: 139.2 g, HPLC purity: 99.75%, yield: 92.5%, melting point: 130.9° C. to 131.5° C.

(2) The First Recycling 96.4 g of 7-ethyltryptophol (content: 98.0%, scalar quantity: 0.5 mol) and 68.3 g of methyl 3-oxopentanoate (0.525 mol) were added to the above mother liquor. 57.0 g of trimethylchlorosilane (0.525 mol) was added to the constant-pressure dropping funnel, and then slowly added dropwise to the above reaction system at a controlled temperature no more than 20° C. for 4 h. After the dropwise addition was completed, the reaction system reacted overnight (about 18 h) at 20° C. until the content of 7-ethyltryptophol was less than 0.1%, as measured by HPLC. Then the reaction solution was cooled to 10° C. and kept at this temperature for 1 h, and filtered. The filter cake was rinsed with 25 g of cold methanol, and the mother liquor was to be treated.

The filter cake was rinsed with 150 g of 5% sodium bicarbonate solution and 50 g of water, and dried to obtain a white solid product: 150.3 g, HPLC purity: 99.78%, yield: 99.9%, melting point: 130.8° C. to 131.1° C.

(3) The Second Recycling 25 g of methanol, 96.4 g of 7-ethyltryptophol (content: 98.0%, scalar quantity: 0.5 mol) and 68.3 g of methyl 3-oxopentanoate (0.525 mol) were added to the above mother liquor. 57.0 g of trimethylchlorosilane (0.525 mol) was added to the constant-pressure dropping funnel, and then slowly added dropwise to the above reaction system at a controlled temperature no more than 20° C. for 4 h. After the dropwise addition was completed, the reaction system reacted overnight (about 18 h) at 22° C. until the content of 7-ethyltryptophol was less than 0.1%, as measured by HPLC. Then the reaction solution was cooled to 12° C. and kept at this temperature for 1 h, and filtered. The filter cake was rinsed with 25 g of cold methanol, and the mother liquor was to be treated.

The filter cake was rinsed with 150 g of 5% sodium bicarbonate solution and 50 g of water, and dried to obtain a white solid product: 150.6 g, HPLC purity: 99.80%, yield: 100.1%, melting point: 130.6° C. to 131.2° C.

Example 3

Trimethylbromosilane was used as catalyst and dehydrating agent.

At 18° C., 283.5 g of methanol, 96.4 g of 7-ethyltryptophol (content: 98.0%, scalar quantity: 0.5 mol) and 71.5 g of methyl 3-oxopentanoate (0.55 mol) were added to a four-necked flask equipped with a thermometer, a mechanically-agitated drying tube and a constant-pressure dropping funnel. 82.5 g of trimethylbromosilane (0.55 mol) was added to the constant-pressure dropping funnel, and then slowly added dropwise to the above reaction system at a controlled temperature no more than 20° C. for 4 h. After the dropwise addition was completed, the reaction system reacted overnight (about 18 h) at 22° C. until the content of 7-ethyltryptophol was less than 0.1%, as measured by HPLC. Then the reaction solution was cooled to 12° C. and kept at this temperature for 1 h, and filtered. The filter cake was rinsed with 25 g of cold methanol, and the mother liquor was to be treated.

The filter cake was rinsed with 150 g of 5% sodium bicarbonate solution, and dried to obtain a white solid product: 138.6 g, HPLC purity: 99.59%, yield: 92.1%, melting point: 130.7° C. to 131.6° C.

Structural Identification of the Product:

HNMR ($^1$H-NMR) (CDCl$_3$, 500 MHz): δ 0.83 (t, 3H, CH$_3$), 1.39 (t, 3H, CH$_3$), 2.00 (q, 1H, ½CH$_2$), 2.17 (q, 1H, ½CH$_2$), 2.73-3.04 (m, 6H, 3CH$_2$), 3.72 (s, 3H, OCH$_3$), 3.91-4.07 (m, 2H, CH$_2$), 7.00-7.37 (m, 3H, ph-H), 9.05 (s, 1H, NH), mass spectrum (ESI-MS): 302 (M+1), elemental analysis (C$_{18}$H$_{23}$NO$_3$, %) (measured value/calculated value): C, 71.68/71.73; H, 7.72/7.69; N, 4.61/4.65, infrared spectrum (IR, KBr, cm$^{-1}$): 3380, 2968, 1709, 1443, 1316, 1238, 1173, 1079, 1018, 911, 745.

The mother liquor was concentrated to no flow, slurried with 40 g of methanol at 40° C. for 1 h, cooled to 12° C. and kept at this temperature for 1 h, and filtered. The filter cake was rinsed with 2.5 g of cold methanol, 15 g of 5% sodium bicarbonate solution and 5 g of water, and then dried to obtain a white solid product: 8.9 g, HPLC purity: 99.86%, melting point: 130.5° C. to 131.3° C.

The combined production was 147.5 g, with a yield of 98.0%.

Example 4

Trimethylbromosilane was used as catalyst and dehydrating agent, and the mother liquor was recycled.

(1) The First Batch of Materials

At 18° C., 283.5 g of methanol, 96.4 g of 7-ethyltryptophol (content: 98.0%, scalar quantity: 0.5 mol) and 71.5 g of methyl 3-oxopentanoate (0.55 mol) were added to a four-necked flask equipped with a thermometer, a mechanically-agitated drying tube and a constant-pressure dropping funnel. 82.5 g of trimethylbromosilane (0.55 mol) was added to the constant-pressure dropping funnel, and then slowly added dropwise to the above reaction system at a controlled temperature no more than 20° C. for 4 h. After the dropwise addition was completed, the reaction system reacted overnight (about 18 h) at 22° C. until the content of 7-ethyltryptophol was less than 0.1%, as measured by HPLC. Then the reaction solution was cooled to 12° C. and kept at this temperature for 1 h, and filtered. The mother liquor was to be treated.

The filter cake was rinsed with 150 g of 5% sodium bicarbonate solution and 50 g of water, and dried to obtain a white solid product: 139.1 g, HPLC purity: 99.82%, yield: 92.4%, melting point: 130.5° C. to 131.2° C.

(2) The First Recycling 96.4 g of 7-ethyltryptophol (content: 98.0%, scalar quantity: 0.5 mol) and 68.3 g of methyl 3-oxopentanoate (0.525 mol) were added to the above mother liquor. 80.3 g of trimethylbromosilane (0.525 mol) was added to the constant-pressure dropping funnel, and then slowly added dropwise to the above reaction system at a controlled temperature no more than 20° C. for 4 h. After the dropwise addition was completed, the reaction system reacted overnight (about 18 h) at 22° C. until the content of 7-ethyltryptophol was less than 0.1%, as measured by HPLC. Then the reaction solution was cooled to 10° C. and kept at this temperature for 1 h, and filtered. The filter cake was rinsed with 25 g of cold methanol, and the mother liquor was to be treated.

The filter cake was rinsed with 150 g of 5% sodium bicarbonate solution and 50 g of water, and dried to obtain a white solid product: 150.1 g, HPLC purity: 99.85%, yield: 99.7%, melting point: 130.8° C. to 131.5° C.

(3) The Second Recycling 25 g of methanol, 96.4 g of 7-ethyltryptophol (content: 98.0%, scalar quantity: 0.5 mol) and 68.3 g of methyl 3-oxopentanoate (0.525 mol) were added to the above mother liquor. 80.3 g of trimethylbromosilane (0.525 mol) was added to the constant-pressure dropping funnel, and then slowly added dropwise to the above reaction system at a controlled temperature no more than 20° C. for 4 h. After the dropwise addition was completed, the reaction system reacted overnight (about 18 h) at 22° C. until the content of 7-ethyltryptophol was less than 0.1%, as measured by HPLC. Then the reaction solution was cooled to 12° C. and kept at this temperature for 1 h, and filtered. The filter cake was rinsed with 25 g of cold methanol, and the mother liquor was to be treated.

The filter cake was rinsed with 150 g of 5% sodium bicarbonate solution and 50 g of water, and dried to obtain a white solid product: 150.4 g, HPLC purity: 99.76%, yield: 99.9%, melting point: 130.6° C. to 131.5° C.

It can be seen from above examples that in the present invention, etodolac methyl ester is prepared by adopting 7-ethyltryptophol and methyl 3-oxopentanoate as raw materials, methanol as a solvent, and trimethylhalosilane as a dehydrating agent and catalyst, with a high yield. The method can achieve almost quantitative yield by continuously recycling the mother liquor, and does not use concentrated sulfuric acid that is extremely harmful and tends to cause product oxidation.

The above descriptions are merely preferred implementations of the present invention. It should be noted that a person of ordinary skill in the art may further make several improvements and modifications without departing from the principle of the present invention. Such improvements and modifications should be deemed as falling within the protection scope of the present invention.

What is claimed is:

1. A method for preparing etodolac methyl ester, wherein the method comprises the following steps:
   (1) raw materials are mixed and subjected to cyclization reaction at 20° C. to 25° C. to obtain a reaction solution, wherein the raw materials comprise 7-ethyltryptophol, methyl 3-oxopentanoate, trimethylhalosilane and methanol, excluding concentrated sulfuric acid, and the trimethylhalosilane is trimethylchlorosilane or trimethylbromosilane; and
   (2) the reaction solution is cooled to 10° C. to 15° C., and then filtered to obtain etodolac methyl ester and a mother liquor.

2. The method according to claim 1, wherein the mixing in step (1) is conducted by adding trimethylhalosilane dropwise to a mixed solution of 7-ethyltryptophol, methyl 3-oxopentanoate and methanol at 15° C. to 20° C.

3. The method according to claim 2, wherein the dropwise adding is performed at a rate of 20% to 30% of the total amount of trimethylhalosilane per hour.

4. The method according to claim 1, wherein, in step (1), 7-ethyltryptophol, methyl 3-oxopentanoate and trimethylhalosilane are used at a mole ratio of 1:(1-1.3):(1-1.3).

5. The method according to claim 1, wherein, in step (1), the cyclization reaction is conducted for 15 h to 18 h.

6. The method according to claim 1, wherein, after a mother liquor is obtained in step (2), the method further comprises: subjecting the mother liquor to post-treatment to obtain etodolac methyl ester; or
recycling the mother liquor in step (1).

7. The method according to claim 6, wherein the post-treatment comprises the following steps:
(a) the mother liquor is concentrated and then slurried with methanol at 30° C. to 45° C. to obtain a slurry; and
(b) the slurry is cooled to 10° C. to 15° C., and then filtered to obtain etodolac methyl ester.

8. The method according to claim 1, wherein, after the filtering in step (2) and step (b), the method further independently comprises: rinsing and drying the obtained solid to obtain etodolac methyl ester, wherein the rinsing is conducted with methanol, a sodium bicarbonate aqueous solution and water in sequence.

9. The method according to claim 8, wherein, after the solid obtained in step (2) is rinsed with methanol, the resulting rinse solution is added to the mother liquor.

10. The method according to claim 1, wherein the trimethylhalosilane is recovered by the following method:
the mother liquor is neutralized to neutrality and then subjected to rectification to obtain hexamethyldisiloxane; and the hexamethyldisiloxane is mixed with hydrogen halide for halogenation to obtain trimethylhalosilane, wherein the hydrogen halide is hydrogen chloride or hydrogen bromide.

11. The method according to claim 2, wherein, in step (1), 7-ethyltryptophol, methyl 3-oxopentanoate and trimethylhalosilane are used at a mole ratio of 1:(1-1.3):(1-1.3).

12. The method according to claim 2, wherein, in step (1), the cyclization reaction is conducted for 15 h to 18 h.

13. The method according to claim 7, wherein, after the filtering in step (2) and step (b), the method further independently comprises: rinsing and drying the obtained solid to obtain etodolac methyl ester, wherein the rinsing is conducted with methanol, a sodium bicarbonate aqueous solution and water in sequence.

14. The method according to claim 13, wherein, after the solid obtained in step (2) is rinsed with methanol, the resulting rinse solution is added to the mother liquor.

* * * * *